United States Patent [19]

Borodulin et al.

[11] Patent Number: 5,190,557
[45] Date of Patent: Mar. 2, 1993

[54] VIBRATORY METHOD AND INSTRUMENT FOR EXTRACTING STONES FROM URINARY TRACT

[75] Inventors: German Borodulin; Maxim Persidsky, both of San Francisco; Alexander Shkolnik, San Mateo; Marshall Stoller, San Francisco, all of Calif.

[73] Assignee: Urological Instrument Research, Inc., San Francisco, Calif.

[21] Appl. No.: 771,396

[22] Filed: Oct. 3, 1991

[51] Int. Cl.⁵ .............................................. A61B 8/00
[52] U.S. Cl. ...................................... 606/127; 606/1; 606/128; 604/22
[58] Field of Search .................... 128/737; 604/22, 27, 604/28, 53, 93, 264, 280, 281, 283; 606/1, 127, 128, 169

[56] References Cited

U.S. PATENT DOCUMENTS

| | | | |
|---|---|---|---|
| 2,943,626 | 7/1960 | Dormia | 606/127 |
| 4,295,464 | 10/1981 | Shihata | 604/27 |
| 4,504,264 | 3/1985 | Kelman | 604/28 |
| 4,612,931 | 9/1986 | Dormia | 606/127 |
| 4,625,726 | 12/1986 | Duthoy | 606/127 |
| 4,741,335 | 5/1988 | Okada | 606/127 |
| 4,748,971 | 6/1988 | Borodulin et al. | 606/127 |
| 4,790,812 | 12/1988 | Hawkins, Jr. et al. | 604/27 |
| 4,898,574 | 2/1990 | Uchiyama et al. | 604/22 |

FOREIGN PATENT DOCUMENTS

| | | | |
|---|---|---|---|
| 0148304 | 7/1985 | European Pat. Off. | 606/128 |
| 0198703 | 10/1986 | European Pat. Off. | 606/128 |
| 2604024 | 8/1976 | Fed. Rep. of Germany | 606/127 |
| 0480410 | 11/1975 | U.S.S.R. | 606/127 |
| 2066668 | 7/1981 | United Kingdom | 606/127 |
| 2116046 | 9/1983 | United Kingdom | 606/128 |

Primary Examiner—Stephen C. Pellegrino
Assistant Examiner—Glenn Dawson

[57] ABSTRACT

An instrument for extracting stones from the urinary tract of a patient comprising a urological catheter (12) and a stone-extracting basket (26) formed from resilient wires and slidingly inserted into catheter (12). The instrument has a drive unit (18) which is connected to the basket via a rod (22). Drive unit (18) transmits to the rod rotation and axial vibrations, which in turn are transmitted to the basket. When rod (22) rotates, curved portion (21) generates radial vibrations which are transmitted to the basket. In order to prevent basket (26) from rotating, but to transmit to it only axial and radial vibrations, rod (24) is connected to basket (26) through a spherical joint (42). On its front end the basket has a filiform (38) which facilitates insertion of the instrument into the urinary tract. In use, after insertion of the catheter to a position in which the basket is aligned with the location of the stone, the basket is released from the catheter and expands. The urologist maneuvers the basket so that the stone is caught inside the basket, and then the basket is pulled back into the catheter to prevent the stone from falling out of the basket. To facilitate extraction, the drive unit is then energized, imparting axial and radial vibrations to the basket, which under these conditions is gradually withdrawn from the patient's body together with the stone caught into the basket.

15 Claims, 2 Drawing Sheets

VIBRATORY METHOD AND INSTRUMENT FOR EXTRACTING STONES FROM URINARY TRACT

FIELD OF THE INVENTION

The present invention relates to the field of urology, and more particularly to an instrument and method for extracting stones from the urinary tract.

BACKGROUND—DESCRIPTION OF PRIOR ART TECHNIQUE

In a human body, urine flows from the kidney through the ureter to the urinary bladder, and then exits a person's body via the urethra. This system can be intermittently or permanently blocked by a hard stone-like material which is known as calculus. Such blockage can be painful and dangerous, since it restricts the flow of urine through the ureter. An obstructed ureter in the presence of infection may result in sepsis and death. Urinary calculi may pass spontaneously, but not always. Especially in those cases when the stone is large, jagged, or has an unfavorable location, surgical intervention may be required for successful extraction.

In general, the number of hospital admissions for removal of urinary calculi or stones averages about 0.1% of the population. Among the above-mentioned patients, a considerable percentage (2.9 admissions per 1000 hospital admissions) belongs to patients with ureteral stones.

Different types of intervention are now used in urology to facilitate successful passage or extraction of urinary calculi, including extracorporeal shockwave lithotripsy, ultrasonic, laser and electrohydraulic lithotripsy, and stone basketing techniques. Basket extraction remains simple and reliable, especially with stones in the distal ureter.

The most common stone extractor is made from a cable having a wire basket at one end of the cable with a relatively short, somewhat flexible rod-like end element, known as a filiform. The filiform is located on the distal end of the cable. The basket is usually made of several, e.g., four, equally spaced wires, which are sufficiently rigid to hold a large, V-shaped configuration (see U.S. Pat. No. 4,625,726 to Everette J. Duthoy, 1986). The wires and basket are located in a tubular catheter, so that only the filiform protrudes through the distal end of the catheter, while the basket portion is held inside the catheter in a contracted form.

In operation, the catheter containing the rod and the basket is inserted into the bladder through an endoscope placed in the urethra. In this case, the catheter is passed into the bladder under visual observation through the ureteral orifice. The catheter is then retracted so that the wires which form the basket are released, expanding the basket under the springing action of the rods. The basket is then maneuvered so that the stone is caught inside the basket through spaces between the wires, and then the rod is pulled toward the catheter; as this happens the and spaces or windows between the wires are reduced to dimensions smaller than the size of the stone. In this position the stone cannot fall out from the basket and is removed from the urinary tract by pulling the catheter and the basket from the patient's body.

However, the stone may be impacted in some place of the ureter due to edema, inflammation, or spasm, thus complicating the passage of the extractor, as well as the subsequent removal of the stone. Because an irregular configuration and sharp edges of the stone, or entrapment of the ureteral mucosa with the basket may injure or cut the endothelium during extraction, it is necessary to exercise great care in conducting this procedure.

OBJECTS OF THE INVENTION

It is an object of the invention to provide an instrument and a method for extracting impacted or lodged stones from the urinary tract with a reduced chance of complications or injuries to the ureteral walls. It is another object to facilitate stone extraction with reduced friction between the inner walls of the canal of the patient's urinary tract and the stone extracting instrument. Still another object is to provide a new and efficient method for stone extraction in combination with the application of low-frequency vibrations to the walls of the ureter.

These and other objects and features of the invention will be more clearly understood after consideration of the ensuing description and accompanying drawings.

DRAWINGS

FIG. 1-7—DESCRIPTION OF THE INVENTION

A new method for the extraction of stones from the ureter is based on the fact that extraction is carried out simultaneously with the application of low-frequency vibrations to the walls of the ureter by means of a tubular catheter which is used as a guide for the cable that carries the stone extraction basket. The vibratory action of the catheter and the extraction movement of the basket are accompanied by low-frequency axial vibrations of the basket and combined radial and axial vibration of the rod. During extraction, the vibration functions as "lubrication" in that it eases the withdrawal of the instrument holding the stone caught in the basket. Low-frequency vibration applied to the inner surface of the ureteral wall may markedly decrease the contraction force of the ureteral smooth muscles. These vibrations also have a pain-relieving effect, making extraction less painful and less traumatic.

The method of the invention can be carried out with the use of an instrument of the type shown in FIGS. 1–9.

Figure 1:
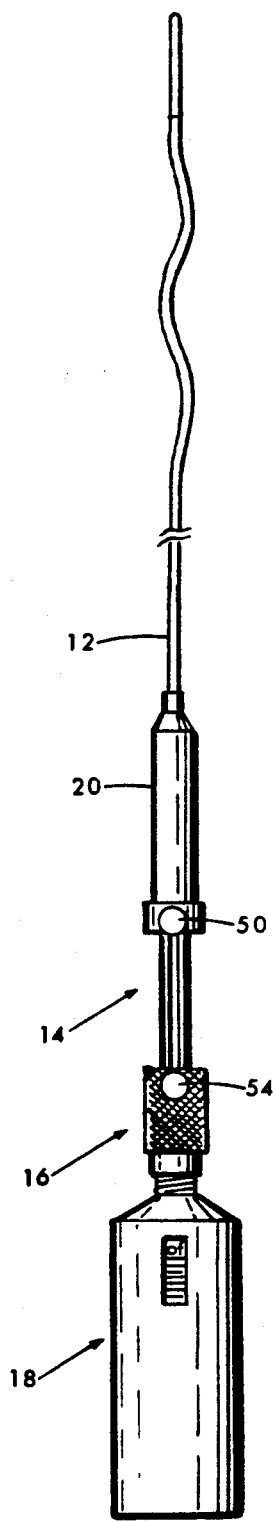
FIG. 1 is a general longitudinal sectional view of the instrument of the invention with a basket in a contracted state inside a catheter.

FIG. 1 is a general sectional view of a stone extracting instrument 10 which consists of a conventional tubular catheter 12, a rod guide unit 14, a connection unit 16, and a drive unit 18.

Figure 2:
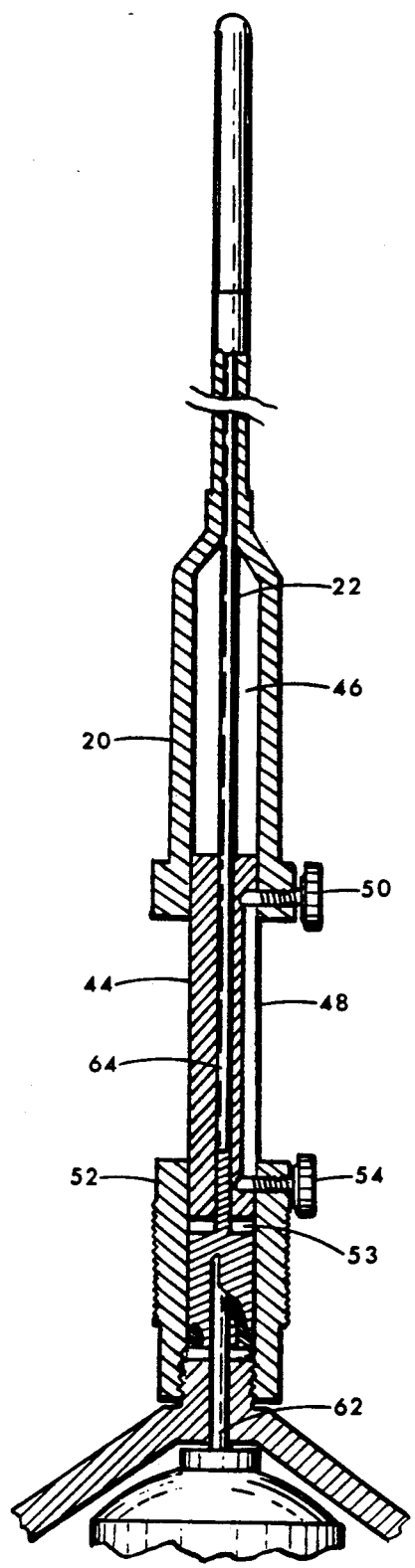
FIG. 2 is a longitudinal sectional view showing a catheter guide unit and a connection between the catheter and a drive unit.

Catheter 12 comprises a transparent flexible tubular element of sufficient rigidity to be inserted into the ureter through the urethra and bladder (not shown). A proximal end 20 of catheter 12 has an enlarged diameter and forms a hollow tubular member (FIG. 2). Proximal end 20 can be connected to the remaining part of the catheter or molded integrally therewith.

Figure 3:
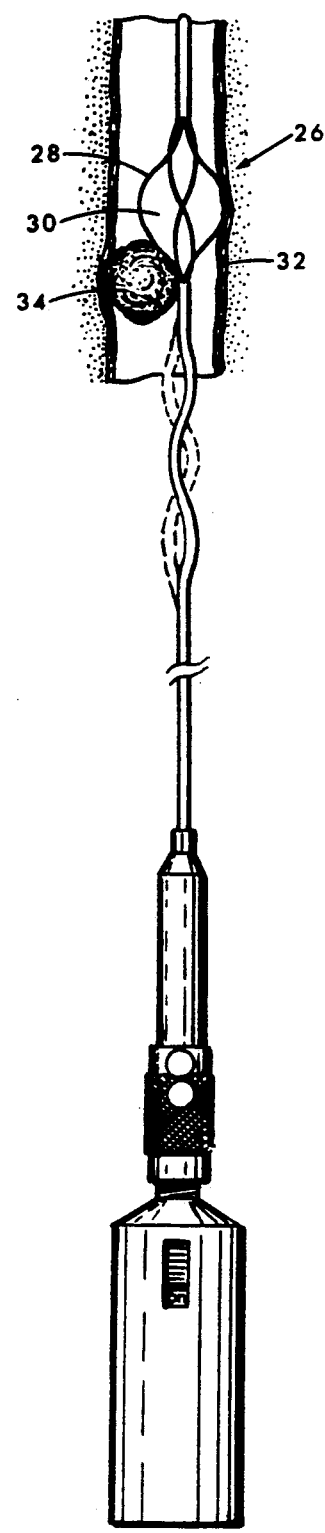
FIG. 3 is a view of the same instrument as is shown in FIG. 1, with the basket in an expanded state after passing the stone.
Figure 4:
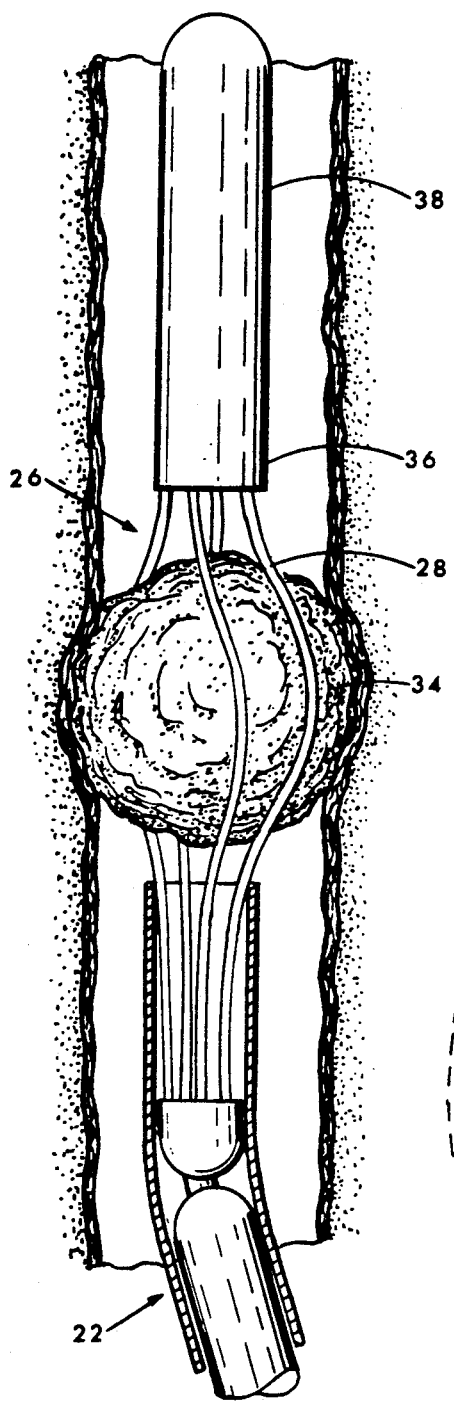
FIG. 4 is a view showing a stone caught in the basket.

A rigid flexible rod 22 is inserted into catheter 12 so that it can be guided axially inside the catheter with respect to the latter in a manner described in detail later. A distal end 24 of rod 22 is connected to a stone-extraction basket 26. The basket has springing properties and expands automatically into the state shown in FIG. 3. It can, however, be constricted when it is pulled into catheter 12 (FIG. 1). A portion 21 of rod 22 beneath basket 26, i.e., in the direction closer to drive unit 18, is twisted in a sinusoidal shape, as shown in FIG. 3. As catheter 12 is made of a resilient material such as plastic, it assumes the twisted shape of the rod on the length of its portion 21.

As shown in FIG. 3, basket 26 is composed of several, for example, four, springing wires 28 which have natural resiliency and are connected at their front and rear ends. Windows 30 are formed between adjacent wires. When the basket is constricted, e.g., by pulling it into catheter 12, windows 30 are reduced in size, and when the basket is released from the catheter (FIG. 3), it expands due to its natural resiliency, and windows 30 are increased in diameter. In the position shown in FIG. 1, basket 26 is completely inserted into the distal end of catheter 12, so that catheter 12 may be easily inserted into the urinary tract 32 of a patient, passing a calculus 34 in order to catch it in the basket. When it is necessary to expand the basket, rod 22 is pushed forward with respect to the catheter, so that basket 26 protrudes from distal end 24 of catheter 12 and expands radially into a rhomboidal configuration shown in FIG. 3. When basket 26 is in an expanded state, the spaces between wires 28 are increased so that basket windows 30 are expanded to the limits which allow insertion of a calculus 34 (FIGS. 3 and 4), which will be described in detail later with regard to operation of the device.

Basket 26 has on its proximal end a short pilot rod 38 which is known as a filiform and is used to guide the instrument during its insertion into urinary tract 32. A distal end 40 of basket 26 is connected to rod 22 through a coupling, e.g., a spherical joint 42 (FIG. 5) which allows rotation of rod 24, but maintains basket 26 in a nonrotating state.

It is understood that the above-described construction has been given only as an example, and that the coupling and connection between basket 26 and rod 22 may have any other construction and configuration, provided that it allows the free rotation of basket 26 with respect to rod 22 and transmits axial vibrations from the rod to the basket.

As has been mentioned above, stone extracting instrument 10 has a guide unit 14 which is comprised essentially of proximal end 20 of the catheter. A sleeve 44 (FIG. 2) is inserted into a cavity 46 formed in proximal end 20, which, as has been mentioned above, has an enlarged diameter. Sleeve 44 is slidingly fitted inside cavity 46, so that it can be moved axially inside distal end 20 of catheter 12. A longitudinal slot 48 is formed in the outer surface of sleeve 44. A first lock screw 50 is threaded through the wall of proximal end 20 so that the end of this screw may be inserted into slot 48. When screw 50 is tightened, distal end 20 and, hence, catheter 12 as a whole are locked. Catheter 12 becomes rigidly connected to the front end of sleeve 44, i.e., the basket-facing end. In other words, screw 50 can fix catheter 12 or release it for axial movement with respect to rod 22. The end of sleeve 44 opposite to basket is inserted into a bush 52 and is attached to it by means of a second lock screw 54 which, when screwed into bush 52, also penetrates slot 48 at its end opposite to first screw 50. When second screw 54 is tightened, sleeve 44 is rigidly attached to bush 52, and when second screw 54 is loosened, sleeve 44 is able to slide axially with respect to bush 52, while the end of second screw 54, which still remains in slot 48, prevents relative rotation between the sleeve and bush. In order to allow such relative rotation, second screw 54 should be unscrewed to the extent that its end is removed from the slot. The end of bush 52 opposite to screw 54 has an internal thread 56 formed in a central bore 53 of the bush. By means of thread 56, bush 52 is screwed onto an external thread 58 which is formed on the front end of a housing 60 of drive unit 18. Bush 52 has a central bore 53.

Drive unit 18 has an output shaft 62 (FIG. 2) which rotates concurrently with axial vibrations. Such drive units are available on the market, e.g., for driving tools, such as impact drills, mechanical tooth brushes, etc., which perform rotation and axial movement simultaneously or selectively. Therefore the construction of such drives is beyond the scope of the present invention. Sleeve 44 (FIG. 2) has a through central hole 64, and rod 22 is slidingly fitted in hole 64 and passes through this hole for connection with output shaft 62 of drive unit 18. Although drive 18 unit was described as the one performing rotary and axial movement simultaneously, it is understood that a drive unit which allows selection between rotary and axial motions or between their concurrent and alternating action is also suitable for the invention.

Figure 7:
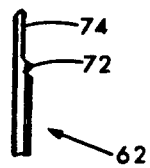
FIG. 7 shows the front end of the output shaft of the drive unit.
Figure 8:
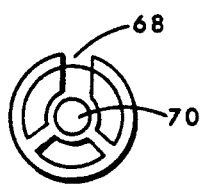
FIG. 8 is a cross-sectional view along line VIII—VIII of FIG. 2.
Figure 9:
FIG. 9 is a perspective view of a locking ring.

Rod 22 is rigidly but removably connected to output shaft 62 of the drive unit through connection unit 16 which is described below. Connection unit 16 (FIG. 6) consists of a cylindrical plug 66 which is slidingly fitted into bore 52 of bush 53. One end of plug 66 is rigidly connected to the rear or distal end of rod 22 or is made integrally therewith. The other end of plug 66 is formed with resilient lugs 68 which in a free state of plug 66 expand outward. A hole 70 is formed between lugs. In a free state of plug 66 this hole has an increased diameter which can be decreased when plug 66 is squeezed and inserted into bore 53 of bush 52. As shown in FIG. 7, which illustrates the end of output shaft 62 of drive unit 18, output shaft 62 has a notch 72 and a pilot end 74. A ring 76 (FIG. 9) with a longitudinal finger 78 is fitted onto output shaft 62 and inserted into bore 53. Finger 78 has a spring-loaded inward-facing projection 80 which in an assembled state of the unit engages the above-mentioned notch 72 of output shaft 62. Thus, when bush 52 is attached to housing 60 through engagement between threads 56 and 58, rod 22 is rigidly connected to output shaft 62 of drive unit 18 through the engagement between projection 80 and notch 72. Furthermore, pilot end 74 has a semicircular cross-section and functions as a key, which is inserted into a conforming semicircular hole in plug 66. In other words, when the drive unit is energized, rotation and reciprocation of its output shaft 62 is transmitted to rod 22

The connection unit of the type described is known and is used, e.g., in a mechanically-driven tooth brush produced by Braun A. G., Germany. It is understood, however, that connection unit 16 was given as an example only and that any other mechanism and principle can be used for connecting rod 22 to output shaft 62 of drive unit 18.

It is recommended for the purpose of the invention that rod 22 have axial vibrations with amplitude between 0 and 2 mm, and that the amplitude of radial vibrations caused by the presence of twisted portion 21 in rod 22 be between 0 and 5 mm. The frequency of axial vibrations should be between 0 and 300 Hz (for axial vibrations). The catheter may have a diameter of about 3 mm.

OPERATION

If drive unit 18 and catheter 12 with guide unit 14 are stored in a disassembled state, prior to use instrument 10 must be assembled. For this purpose, first screw 50 is tightened and second screw 54 is unscrewed so that it is possible to shift sleeve 44 inside bush 52, thus causing cylinder plug 66 to protrude outside bush 52. As a result, lugs 68 of a collet-like rear end of plug 66 expand radially and this increases the diameter of hole 70. A ring 76 is then fitted onto output shaft 62, so that projection 80 of finger 78 is inserted into notch 72 of the output shaft. The output shaft with ring 76 is inserted into hole 70 (FIG. 6) and lugs 68 are then squeezed by pushing sleeve 44 into bush 52, so that inner thread 56 of bush 52 could be screwed onto external thread 58 of drive unit housing 60 and tightened (FIG. 2). When screw 54 is then tightened, catheter 12 with guide unit 14 are connected to drive unit 18. The instrument is now ready for use.

Assume that a patient has a non-impacted calculus somewhere in the urinary tract 32, e.g., in the ureter. Before insertion of instrument 10 into the ureter, it is necessary to switch off the motor of drive unit 18, loosen screw 50, move forward distal end 20 of catheter and, hence, the entire catheter 12, away from drive unit 18 until the part which constitutes basket 26 is firmly closed in the proximal end of catheter 12, but leaving filiform 38 projecting from the catheter (FIG. 1). In this state, instrument 10 is engaged in the physiological canal or duct, e.g., ureter 32, via the urethra and bladder (not shown), where calculus 34 is located. Instrument 10 is inserted as a conventional catheter with the help of filiform 38. When the position of basket 26 is aligned with the position of calculus 34, the urologist, who holds the instrument in one hand by drive unit housing 60, loosens first screw 50 with another hand and moves catheter 12 with respect to rod 22 by pulling enlarged-diameter distal end 20 of catheter 12 toward the drive unit. As a result, basket 26 emerges from the catheter and wires 28 expand radially outward under the effect of springing forces, so that basket 26 assumes a rhomboidal configuration shown in FIG. 3. After the expansion of the basket, first screw 54 may be tightened again. Instrument 10 is then manipulated so that calculus 34 is inserted into basket 26 through one of windows 30 between wires 28. After calculus 34 is caught, basket 26 is returned rearward into the catheter, so that the radial dimensions of basket 26 are reduced, windows 30 between wires 28 decrease, and calculus 34 is trapped inside the basket and cannot be dislodged from the latter.

Figure 5:
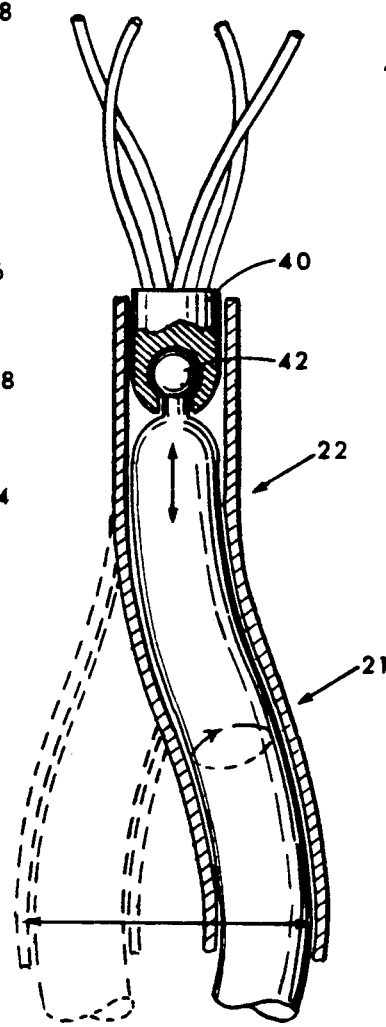
FIG. 5 is a fragmentary longitudinal sectional view of the instrument showing the connection of the basket to a rotating and reciprocating rod.
Figure 6:
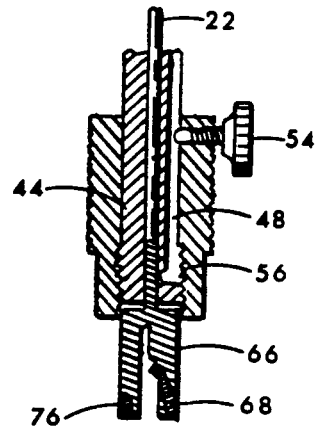
FIG. 6 shows the connecting parts in greater detail.

Drive unit 18 is then switched on. When drive unit is on, its output shaft 62 begins to rotate and vibrate axially. The rotation of output shaft 62 is transmitted to rod 22, which also begins to rotate. Basket 26 with the calculus, however, is not rotated due to the provision of spherical joint 42. As has been mentioned above, simultaneously with rotation, rod 22 executes low-frequency axial vibrations. At the same time, the provision of twisted portion 21 causes radial vibration of the rod during its rotation (FIG. 5). These radial vibrations are transmitted through catheter 12 to the walls of ureter 32. Vibrations applied to the ureter wall beneath the calculus in combination with axial vibrations of basket 28 prevent the spasm of the ureter and at the same time facilitate withdrawal of the calculus. Under these conditions, instrument 10 is slowly extracted from the patient's body together with calculus 34. In addition, the vibrations alleviate pain and act as a "lubricant" which reduces friction between walls of the duct and the calculus, thus facilitating its removal. Radial vibrations of the duct walls from the proximal end of catheter 12 not only facilitate the extraction of the calculus, but also produce a therapeutic, i.e., massaging effect.

In case of removal of a lodged stone, where the insertion of the instrument may cause a problem, it can be inserted with drive unit 18 in an operating or axially vibrating condition so that the proximal end of catheter 12 will vibrate and therefore can more easily pass the stone. During insertion, however, the vibrations are only axial and the basket still remains inside the catheter.

Thus, it has been shown that the present invention provides an instrument and a method for extracting stones from the urinary tract without danger of injury or cutting the inner walls of the duct. The invention also facilitates removal of stones from the ureter and performs the stone extraction with reduced friction between the inner walls of the canal of the patient's urinary tract and the stone extracting instrument. Apart from the improved device, the invention also provides an efficient method for stone extraction through the application of low-frequency vibrations to the walls of the ureter concurrently with the stone extraction operation.

SYNOPSIS, RAMIFICATIONS AND SCOPE

We have just shown and described a simple device and a method for extracting stones from urinary tract which is simple in construction, and reliable in operation.

Although the device has been shown and described in specific embodiments thereof, many modifications and changes can be made within the scope of the invention. For example, basket 26 can be formed by a smaller or greater number of wires than four, as shown in the above description; twisted portion 21 may have different profile than sinusoidal and may comprise, e.g., a crank-like portion with unbalanced mass creating radial vibrations; the drive unit may comprise any axial vibrator combined with a rotation motion. The connection between rod 22 and output shaft 62 of the drive unit also may be executed in many different ways, e.g., it may be a snapping connection, a spring-loaded-ball-and-hole connection, a hook-and-loop connection, etc. All parts of the instrument can be made from other materials than those specified above and may have other configurations. Although the invention has been illustrated with reference to the case of extraction of calculus from the ureter, it is understood that the same instrument and the same method are applicable for extracting any foreign matter from any lumen of a human body, or any other duct. Connection between rod 22 and basket 26 was shown as a spherical joint. It is understood that it can be a connection through a coupling with independent rotation of input and output shafts of the coupling. A drive unit may be one capable of performing rotary motion concurrently with axial vibration, or either axial or rotary movements selectively.

Therefore, the scope of the invention should be determined not by the examples given but by the appended claims and their legal equivalents.

We claim:

1. A method for extracting a foreign solid body from a duct, comprising the steps of:
providing an instrument for extracting stones from the urinary tract with a stone catcher of a flexible nature having windows and capable of performing low-frequency vibrations, said stone catcher being confined in a catheter in a contracted state and being expanded radially, increasing said windows, when it protrudes from said tube to such an extent that a calculus can pass into said catcher through one of said windows, said instrument having drive means for imparting said low-frequency vibrations to said stone catcher;
wherein said drive means for said stone catcher comprises a motor with an output element which performs rotary motions combined with axial vibrations, and a rod-like element which is inserted into said catheter and passes through said catheter connecting said stone basket to said output element of said motor, said rod-like element having a twisted portion, which during the rotation of said rod-like element generates radial vibrations transmitted to said stone basket; wherein said stone catcher is connected to said rod-like element through a coupling member, said coupling member having means to provide free rotation of said rod-like element with respect to said stone catcher and to restrict said rod-like element and said stone catcher against axial movement with respect to each other;
inserting said instrument into the urinary tract of a patient having a calculus in said urinary tract;
aligning the position of said stone catcher with said calculus;
expanding said stone catcher by protruding it from said catheter;
catching said calculus into said stone catcher in its expanded state;
contracting said stone catcher by pulling it in the direction of said catheter to reduce the size of said stone catcher enough to grasp said calculus;
energizing said drive means of said instrument for imparting said low-frequency vibrations to said stone catcher;
extracting said instrument from the urinary tract and from the body of said patient while maintaining the stone catcher under the action of said low-frequency axial vibrations; and
deenergizing said driving means after extraction of said instrument from the body of said patient.

2. The method of claim 1 wherein said stone catcher is composed of at least three resilient wires having front and rear ends formed into a basket-like configuration by being connected at their front and rear ends, said windows being formed between adjacent wires so that when said basket is constricted, said windows are reduced in size, and when said basket is released from constriction, it expands radially due to its natural resiliency, and said windows are increased in size.

3. The method of claim 2 wherein said low-frequency vibrations are composite and consist of said axial vibrations combined with said radial vibrations.

4. The method of claim 1 wherein said twisted portion has a sinusoidal shape.

5. The method of claim 4 wherein said instrument has means for shifting said stone catcher axially with respect to said catheter to the extent that said catcher can be either expanded or confined within said catheter, and means for locking said catcher either in said expanded or in said constricted state.

6. The method of claim 5 where said catheter has a proximal end insertable into said urinary tract and a distal end having a diameter greater than said proximal end, said catcher shifting means comprises a distal end of said catheter, a sleeve slidingly fitted in said distal end of said catheter, a means for rigidly fixing said sleeve to said distal end of said catheter, said sleeve having a bore, said rod-like element being slidingly fitted in said bore, said locking means comprising a screw threaded through a threaded hole formed in the wall of said distal end of said catheter, said sleeve having an outer surface with a longitudinal groove to receive said screw when said screw is tightened and threaded into said distal end of said catheter.

7. A method for extracting a stone from a urinary tract of a patient, comprising the steps of:
providing an instrument for extracting stones from the urinary tract with a stone catcher of a flexible nature having windows and capable of performing low-frequency axial vibrations, said stone catcher being confined in a catheter in a contracted state and being expanded radially, increasing said windows when it protrudes from said tube to such an extent that a calculus can pass into said catcher through one of said windows, said instrument having drive means for imparting said axial low-frequency vibrations to said stone catcher.
wherein said drive means for said stone catcher comprises: a motor with an output element which performs rotary motions combined with axial vibrations, and a rod-like element which is inserted into said catheter and passes through said catheter connecting said stone catcher to said output element of said motor, wherein said stone catcher is connected to said rod-like element through a coupling member, said coupling member having means to provide free relative rotation of said rod-like element with respect to said stone catcher, but to restrict said rod-like element and said stone catcher against axial movement with respect to each other;
energizing said drive means of said instrument for imparting said low-frequency axial vibrations to said stone catcher;
inserting said instrument into the urinary tract of a patient having a calculus in said urinary tract, while said drive unit is energized and said catheter is confined in said contracted state;
expanding said stone catcher by protruding it from said catheter;
aligning the position of said stone catcher in its expanded state with said calculus;
catching said calculus into said catcher in its expanded state;
contracting said stone catcher by pulling it in the direction of said catheter to reduce it in size enough to grasp said calculus;

extracting said instrument from the urinary tract and from the body of said patient while maintaining the stone catcher in the state of vibratory motion; and deenergizing said driving means after extraction of said instrument from the body of said patient.

8. An instrument for extracting stones from the urinary tract of a patient comprising:
a flexible tubular urological catheter;
a stone catcher of flexible nature having windows, said stone catcher being able to be contracted to reduce the size of said windows, and to be expanded due to its natural flexibility to enlarge said windows, said stone catcher being slidingly inserted into said catheter so that it is in a contracted state when it is pulled into said catheter and is in a radially expanded state when it protrudes from said catheter, in said expanded state said windows being increased to a size that said stone can pass into said stone catcher through one of said windows;
a drive means for imparting composite low-frequency vibrations to said stone catcher, said drive means capable of performing rotary motions and vibratory motions simultaneously or selectively; and means for connecting said drive means with said stone catcher wherein said drive means for said stone catcher comprises: a motor with an output element which performs rotary motions combined with axial vibrations, and a rod-like element which is inserted into said catheter and passes through said catheter connecting said stone catcher to said output element of said motor, wherein said stone catcher is connected to said rod-like element through a coupling member, said coupling member having means to provide free relative rotation of said rod-like element with respect to said stone catcher, but to restrict said rod-like element and said stone catcher against axial movement with respect to each other.

9. The instrument of claim 8 wherein said composite vibrations are said axial vibrations combined with radial vibrations.

10. The instrument of claim 9 wherein said stone catcher is composed of at least three resilient wires having front and rear ends, said wires being formed into a basket-like configuration by being connected at said front ends and at said rear ends, said windows being formed between adjacent wires, so that when said basket is constricted, said windows are reduced in size, and when said basket is released from constriction, it expands radially due to its natural resiliency, and said windows are increased in diameter, said basket being connected to a filiform at said front ends.

11. The instrument of claim 10 wherein said instrument has catcher shifting means for shifting said stone catcher axially with respect to said catheter to the extent that said catcher can be either expanded or contracted by being pushed away or pulled towards said catheter respectively, and means for locking said catcher either in said expanded or in said contracted state.

12. The instrument of claim 12 wherein said catheter has a proximal end insertable into said urinary tract and a distal end, said distal end having a diameter greater than said proximal end of said catheter said catheter shifting means comprises said distal end of said catheter, a sleeve slidingly fitted in said distal end of said catheter, and means for rigidly fixing said sleeve to said distal end of said catheter, said sleeve having a bore, said rod-like element being slidingly fitted in said bore, said locking means comprising a screw threaded through a hole formed in the wall of said distal end of said catheter, said sleeve having a longitudinal groove in its outer surface to receive said screw when said screw is tightened and threaded into said distal end of said catheter.

13. The instrument of claim 12 wherein said rod-like element has a twisted portion, which, when said rod-like element rotates, generates said radial vibrations of said rod.

14. The instrument of claim 13 wherein said twisted portion has a sinusoidal configuration.

15. An instrument for extracting stones from the urinary tract of a patient comprising:
a flexible tubular urological catheter;
a wire basket composed of at least three resilient wires having front ends and rear ends and formed into a basket-like configuration by being connected at said front ends and at said rear ends, windows being formed between adjacent wires, so that when said basket is constricted, said windows are reduced in size, and when said basket is released from constriction, it expands radially due to its natural resiliency, and said windows are increased in size, said basket having a filiform at said front ends;
said wire basket being slidingly inserted into said catheter so that it is in a contracted state when it is pulled into said catheter and is in a radially expanded state when it protrudes from said catheter, in said expanded state said windows being increased to a size that said stone can pass into said basket through one of said windows;
a drive means for imparting to said wire basket composite low-frequency vibrations which are composed of axial low-frequency vibrations and radial low-frequency vibrations; means for connecting said drive means with said wire basket; said drive means for said basket comprises: a motor with an output element which performs rotary motions combined with axial vibrations, and a rod-like element which is inserted into said catheter and passes through said catheter connecting said basket to said output element of said motor, said basket being connected to said rod-like element through a coupling member, said coupling member having means to provide free relative rotation of said rod-like element with respect to said basket, but to restrict said rod-like element and said basket against axial movement with respect to each other; said instrument has means for shifting said basket axially with respect to said catheter to the extent that said basket can be either expanded or confined within said catheter, and means for locking said basket either in said expanded or in said constricted state;
said shifting means comprises a distal end of said catheter, a sleeve slidingly fitted in said distal end of said catheter, a means for rigidly fixing said sleeve to said distal end of said catheter, said sleeve having a bore, said rod-like element being slidingly fitted in said bore, said locking means comprising a screw threaded through a threaded hole formed in the wall of said distal end of said catheter, said sleeve having a longitudinal groove in its outer surface to receive said screw when said screw is tightened and threaded into said distal end of said catheter, said rod-like element has a twisted portion, which when said rod rotates, generates said radial vibrations of said rod.

* * * * *